United States Patent
Meredith et al.

(10) Patent No.: US 9,535,022 B1
(45) Date of Patent: Jan. 3, 2017

(54) COMPOSITE MATERIAL MOISTURE DETECTION

(71) Applicant: The Boeing Company, Chicago, IL (US)

(72) Inventors: Kimberly D. Meredith, Newcastle, WA (US); Morteza Safai, Newcastle, WA (US); Sahrudine Apdalhaliem, Seattle, WA (US)

(73) Assignee: The Boeing Company, Chicago, IL (US)

( * ) Notice: Subject to any disclaimer, the term of this patent is extended or adjusted under 35 U.S.C. 154(b) by 139 days.

(21) Appl. No.: 13/944,571

(22) Filed: Jul. 17, 2013

(51) Int. Cl.
*G01N 27/00* (2006.01)

(52) U.S. Cl.
CPC ..................... *G01N 27/00* (2013.01)

(58) Field of Classification Search
CPC ........ G01N 27/22; G01N 22/04; G01N 27/12; G01N 27/048; G01N 27/00
USPC ................ 324/76.11, 519, 754.28, 658, 634, 640,324/643, 664, 689, 694; 73/29.01, 73–77, 73/24.04, 25.04, 152.06, 152.08; 250/339.1, 250/390.05
See application file for complete search history.

(56) References Cited

U.S. PATENT DOCUMENTS

| | | | | |
|---|---|---|---|---|
| 3,811,087 A | * | 5/1974 | Schmelzer | 324/688 |
| 4,236,109 A | * | 11/1980 | Ingle, Jr. | 324/690 |
| 4,788,853 A | * | 12/1988 | Bell | 73/73 |
| 5,086,279 A | * | 2/1992 | Wochnowski et al. | 324/637 |
| 5,939,888 A | * | 8/1999 | Nelson | 324/640 |
| 2003/0132760 A1 | * | 7/2003 | Bray et al. | 324/637 |
| 2003/0146767 A1 | * | 8/2003 | Steele et al. | 324/640 |
| 2003/0169054 A1 | * | 9/2003 | Rynhart et al. | 324/649 |
| 2004/0189331 A1 | * | 9/2004 | Girshovich | G01N 27/121 324/694 |
| 2005/0179578 A1 | * | 8/2005 | Healy et al. | 342/22 |
| 2008/0223152 A1 | * | 9/2008 | Georgeson et al. | 73/862.041 |
| 2008/0282817 A1 | * | 11/2008 | Breed | 73/865.9 |
| 2010/0066386 A1 | * | 3/2010 | Dos Santos et al. | 324/640 |
| 2011/0169507 A1 | * | 7/2011 | Mershin et al. | 324/634 |

* cited by examiner

*Primary Examiner* — Arleen M Vazquez
*Assistant Examiner* — Lee Rodak
(74) *Attorney, Agent, or Firm* — Kunzler Law Group, PC (57) ABSTRACT

A system for detecting moisture characteristics of a material of a complex structure while the material is in situ or forms part of the complex structure. The system includes at least one moisture detection sensor positioned proximate the material of the complex structure while the material is in situ. The system also includes a controller in data receiving communication with the moisture detection sensor.

13 Claims, 5 Drawing Sheets

COMPOSITE MATERIAL MOISTURE DETECTION

FIELD

This disclosure relates generally to detecting moisture characteristics in materials of a complex structure, and more particularly to the in situ detection of moisture saturation and ingression characteristics in composite materials of aircraft.

BACKGROUND

Moisture ingression into and saturation of materials forming complex structures, such as aircraft, automobiles, boats, buildings, and the like, is a problem faced by complex structure manufacturers. When introduced into the materials of complex structures, moisture can cause structural degradation, arcing, shorting, and an increase in weight. Accordingly, to compensate for the ingression and saturation of moisture in materials of complex structures, the materials are specifically selected and configured to compensate for the negative consequences caused by moisture in the materials.

Moisture detection devices and techniques for complex structures in operation are not available. Therefore, a prediction of the ingression and saturation levels of moisture in materials of a complex structure is based on small material samples or coupons removed from a non-operational complex structure, or pre-manufacturing test samples or coupons. Because material samples being tested for moisture characteristics are ex situ (e.g., taken from a non-operational or destroyed complex structures), manufacturers design the materials of complex structures with unduly conservative predictions or allowances for moisture ingression and saturation levels. Such conservative allowances result in excessive or heavier materials, which increase the overall weight of the complex structure, and can reduce the efficiency of the complex structure.

Moreover, ex situ moisture detection techniques are conducted before or after operation of a complex structure. Accordingly, conventional moisture detection techniques are not equipped to provide moisture detection in real-time for an operational complex structure.

SUMMARY

The subject matter of the present application has been developed in response to the present state of the art, and in particular, in response to the problem of, and the need for, detecting moisture characteristics of a complex structure without destroying the complex system or rendering it inoperable. Accordingly, according to some embodiments, the subject matter of the present application has been developed to provide an apparatus, system, and method for in situ detection of moisture characteristics of a material forming a complex structure in real-time without destruction to the structure, that overcome at least some of the above-discussed shortcomings of prior art techniques.

According to one embodiment, a system for detecting moisture characteristics of a material of a complex structure while the material is in situ or forms part of the complex structure (which means coupled to, positioned on, positioned in, or the like within the complex structure) is described herein. The system includes at least one moisture detection sensor positioned proximate the material of the complex structure while the material is in situ or forms part of the complex structure. The system also includes a controller in data receiving communication with the moisture detection sensor.

In some implementations, the moisture detection sensor is embedded in the material of the complex structure. The moisture detection sensor can include a transmitting portion that transmits an electric field through the material, and a receiving portion that receives the electric field. The transmitting portion can be spaced apart from the receiving portion. The controller may be in data receiving communication with the moisture detection sensor via a wireless connection. The at least one moisture detection sensor can include or be a plurality of moisture detection sensors. The controller determines at least one of a moisture saturation level of the material, a moisture concentration level on a surface of the material, or a moisture ingression point in the material.

According to some implementations, the moisture detection sensor is positioned exteriorly adjacent a first exterior surface of the material. The moisture detection sensor can be movable along the exterior surface of the material. The moisture detection sensor can include a transmitting portion that transmits an electric field through the material, where the transmitting portion is adjacent the exterior surface. Also, the moisture detection sensor can include a receiving portion that receives the electric field, where the receiving portion is adjacent a second exterior surface opposing the first exterior surface. The transmitting portion can be spaced apart from the receiving portion. The moisture detection sensor may also be spaced exteriorly away from the first exterior surface, with the moisture detection sensor including a transmitting portion that transmits a beam of energy, and a receiving portion that receives at least a portion of the beam of energy reflecting off of the material. The beam of energy can include one of an electromagnetic energy field or beam of light. Further, the controller can determine at least one of a moisture concentration level on a surface of the material, a moisture saturation level of the material, or a moisture ingression point in the material.

In certain implementations, the material includes a composite material, and the complex structure can be an aircraft. The at least one sensor can include or be at least one of a capacitance sensor, microwave sensor, or spectra sensor. The controller can be coupled (e.g., removably or fixedly attached) to the complex structure. In some implementations, the at least one moisture detection sensor detects moisture in real-time during operation of the complex structure, and transmits moisture data to the controller in real-time during operation of the complex structure.

According to certain implementations, the at least one moisture detection sensor includes a first moisture detection sensor of a first type and a second moisture detection sensor of a second type different than the first type. The controller can be in data receiving communication with the first and second moisture detection sensors.

In another embodiment, a system for detecting moisture characteristics includes an operational aircraft that has a body made from a composite material. The system also includes at least one moisture detection sensor that detects moisture characteristics of the composite material of the operational aircraft. Further, the system includes a controller that receives moisture characteristics from the at least one moisture detection sensor and determines a condition of the material based on the moisture characteristics. The condition may include at least one of a moisture saturation level of the material, a moisture concentration level on a surface of the material, or a moisture ingression point in the material.

According to yet another embodiment, a method for detecting moisture characteristics of a material of an operational complex structure include positioning a moisture sensing device proximate a material of the operational complex structure while the complex structure is operational. The method also includes detecting moisture characteristics of the material with the moisture sensing device. Further, the method includes determining a condition of the operational complex structure based on the moisture characteristics.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1:
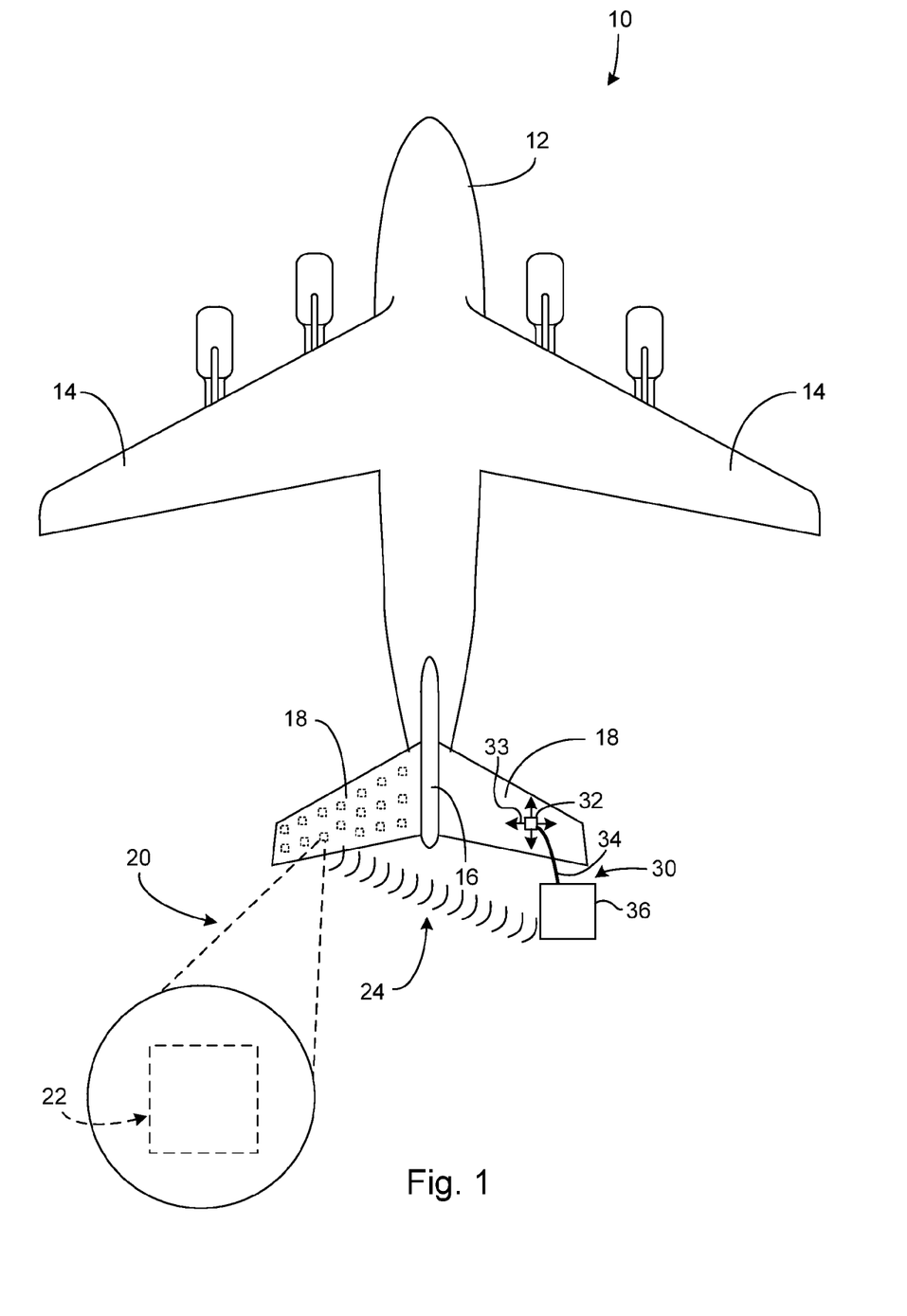
FIG. 1 is a top plan view of an aircraft showing an embedded moisture detection system and a non-embedded moisture detection system according to respective embodiments.

Referring to FIG. 1, one embodiment of a complex structure (e.g., aircraft 10) is shown. The aircraft 10 can be any of various aircraft, such as commercial aircraft used for the transportation of passengers, military aircraft used for military operations, personal aircraft, and the like. Moreover, although the complex structure depicted in the illustrated embodiment is an aircraft, the complex structure can be any of various other complex structures, such as vehicles (e.g., helicopters, boats, spacecraft, automobiles, etc.) or non-mobile complex structures (e.g., buildings, bridges, machinery, etc.). As defined herein, a complex structure includes any multi-component structures in a fully operative state to fulfill the intended purpose of the structure.

The depicted aircraft 10 includes a body or fuselage 12, a pair of wings 14 coupled to and extending from the body 12, a vertical stabilizer 16 coupled to the body, and a pair of horizontal stabilizers 18 coupled to the body and/or the vertical stabilizer. Generally, the body 12, wings 14, vertical stabilizer 16, and horizontal stabilizers 18 of the aircraft each includes an internal frame enveloped by a cover or skin. The cover is coupled to the frame to form an exterior shell of the aircraft. Most commonly, the cover is coupled to the frame using a plurality of fasteners that extend through the cover and engage the frame. For sealing, insulation, electrical conduction, and/or aesthetic effects, one or more additional components can be coupled to an exterior of the cover. For example, one or more coatings can be applied onto the cover. The coatings can include one or more of a sealant coating made from any of various materials, such as an insulation material, dielectric material, a paint coating, a conductive material coating, or a coating embedded with structural components, such as a conductive mesh or layer.

The cover, or additional components coupled to the cover, defines an outermost or exterior surface of the shell of the aircraft 10 exposed to the environment. Similarly, the cover defines an innermost or interior surface of the shell of the aircraft 10. Further, opposing interior surfaces of the shell, along with the frame, may define a hollow interior of the aircraft 10. In some implementations, some portions of the hollow interior include one or more layers of additional materials, such as insulation and the like.

According to one embodiment, an embedded moisture detection system 20 is operable to detect moisture characteristics of material forming the aircraft 10. Referring to FIG. 1, the system 20 includes a moisture detection sensor 22 embedded into the material of the aircraft 10. In the illustrated embodiment, the sensor 22 is embedded into the material forming a horizontal stabilizer 18 of the aircraft 10 while the horizontal stabilizer is in situ (e.g., in position). In other words, the material being tested is not removed from the complex structure, nor is there any destruction to the material or the complex structure, before, during, or after moisture detection of the material by the sensor 22. In other words, the complex structure remains fully operational before, during, and after moisture detection of the material by the sensor 22.

The sensor 22 can be any of various types of moisture detection sensors, such as capacitance sensors, configured to detect the concentration of moisture within the material of the horizontal stabilizer 18. Of course, the embedment of the sensor 22 in the horizontal stabilizer 18 is merely provided as an example of many of various locations of the aircraft in which the sensor 22 could be embedded. For example, in some implementations, the sensor 22 can be embedded in the body 12, a wing 14, the other horizontal stabilizer 18, or the vertical stabilizer 16 to detect the concentration of moisture in the materials forming these respective portions of the aircraft. According to some implementations, the material forming the aircraft 10 is a fibrous composite material (e.g., fiber-reinforced polymers), which can be more susceptible to moisture saturation than other types of materials, such as metal materials.

The embedded sensor 22 is configured to transmit detected moisture concentration information or data to a controller 36 of the system 20 via a wireless signal 24. Accordingly, the sensor 22 may include a wireless transmitter operable to generate a wireless signal encoded with the detected moisture concentration information. Further, the controller 36 includes a wireless receiver operable to receive and decode the wireless signal received from the sensor 22. In some implementations, the controller 36 can be configured to store, process, and/or analyze the moisture concentration data received from the sensor 22. The controller 36 may also be able to transmit the moisture concentration data to a local or remote computing device for initial or additional storage, processing, and/or analyzing. Although the illustrated embodiment depicts a wireless data communication protocol using a wireless signal 24, in other embodiments, the detected moisture concentration data can be communicated using a wired data communication protocol over a wire or cable.

Generally, one or more of the controller 36 and computing device includes instructions for determining moisture characteristics (e.g., moisture saturation or diffusion levels local to the sensor 22) based on the moisture concentration data received from the sensor 22. The controller 36 may also be configured to compare the moisture concentration data or determined moisture characteristics to predetermined thresholds, and generate a moisture condition status indicator or trigger a fault based on the comparison. For example, if the sensor 22 detects an oversaturation of moisture in the material being monitored, the controller 36 may issue a warning or alert a user. In certain embodiments, the sensor(s) 22 and controller 36 are coupled to the aircraft 10, and provide moisture characteristics detection and determination operations while the aircraft is in operation for its intended purpose (e.g., during flight) in real-time. In this manner, the system 20 can be configured to provide a real-time determination and analysis of the moisture characteristics of the material of the aircraft 10 during flight.

Figure 2:
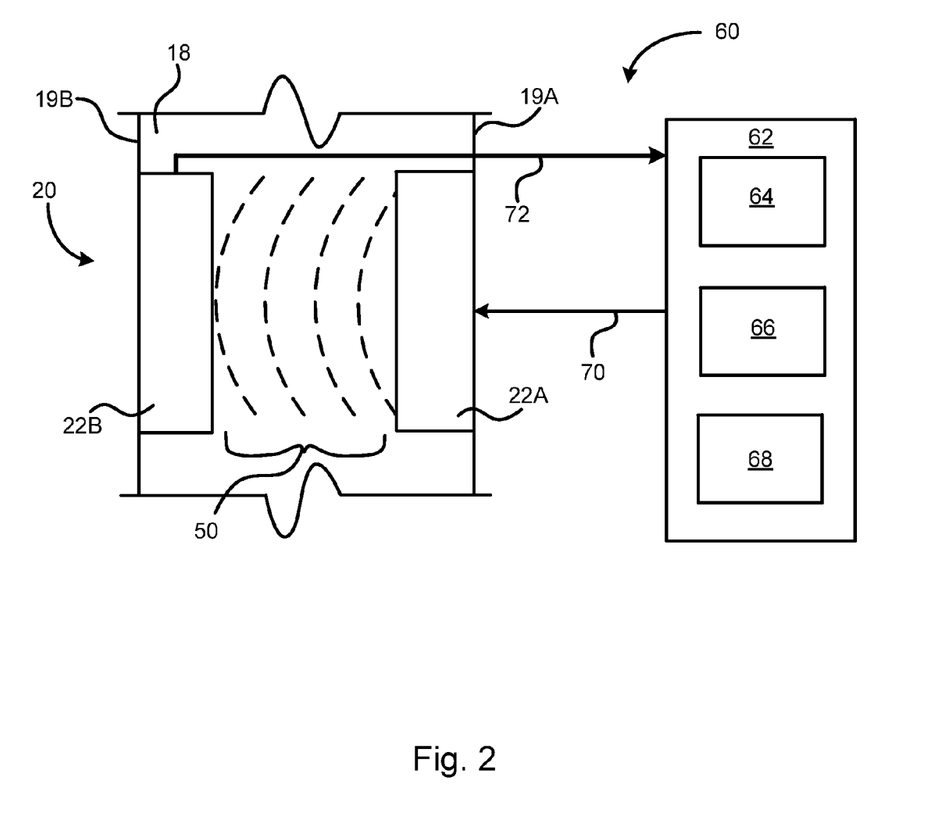
FIG. 2 is a schematic block diagram of an embedded moisture detection system according to one embodiment.

In certain implementations, as shown in FIG. 2, the embedded moisture detection system 20 can include a plurality of moisture detection sensors 22 positioned throughout the shell of the aircraft 10, or concentrated within a specialized location of the aircraft, such as the horizontal stabilizers 18 as shown. Each of the plurality of sensors 22 transmits detected moisture concentration information or data to the controller 36 of the system 20 via a respective wireless signal 24. In such implementations, the controller 36 can store, process, and/or analyze the moisture concentration data received from the sensors 22, or transmit the moisture concentration data to a local or remote computing device for initial or additional storage, processing, and/or analyzing. Because the plurality of sensors 22 can detect the moisture concentration at various locations within a section of the aircraft, the controller 36 can utilize the moisture concentration readings detected by the plurality of sensors 22 to determine advanced moisture characteristics of the material, such as moisture saturation levels and moisture ingression sites, as will be described in more detail below.

As shown in more detail in FIG. 2, according to one embodiment of an embedded moisture detection system 60, the embedded sensor 22 can be a capacitance sensor with a transmitting portion 22A and a receiving portion 22B that is spaced apart from the transmitting portion. Both the transmitting portion 22A and receiving portion 22B are embedded in a material forming a complex structure, which can be a composite material 19 forming the horizontal stabilizer 18 of the aircraft 10. As defined herein, in one implementation, embedment in a material means positioned within and at least partially surrounded by the material. Embedment can, but does not necessarily, mean completely enclosed by the material. Moreover, embedment in a material can also mean at least partially within and inset from an outermost (or innermost) surface of a material (e.g., the outermost exterior surface 19A or innermost interior surface 19B of the horizontal stabilizer 18). Further, in certain implementations, embedment in a material can mean firmly fixed at least partially within a material.

The material 19 in FIG. 2 is shown schematically as being a homogenous single layer of material. However, the material 19 may include multiple layers each made of various materials. For example, in one implementation, the material 19 may be just the cover as a single layer. In other implementations, the material 19 may include the cover, sealant coating, and paint coating as multiple distinct layers applied to each other. According to yet other embodiments, the material 19 may include multiple layers, such as two cover layers, spaced-apart from each other by a hollow interior. In other words, the embedded moisture detection system 60 may be configured to detect moisture characteristics of multiple layers made from the same or different materials.

In one embodiment, the transmitting portion 22A and receiving portion 22B form part of a capacitance sensor 22. The capacitance sensor 22 is configured to detect the concentration of moisture in the material 19 between the transmitting and receiving portions 22A, 22B. As shown, the transmitting portion 22A generates an electric field 50 and transmits the field through the material 19. After passing through the material 19, the transmitted electric field 50 is received by the receiving portion 22B. The characteristics (e.g., wavelength) of the electric field 50 are selected or tuned to correspond with an absorption property of water. In other words, the electric field 50 is configured to be absorbed by water within the material 19, which prevents the reception of the absorbed portion of the electric field by the receiving portion 22B. The difference between the energy or intensity of the electric field 50 transmitted by the transmitting portion 22A and the energy or intensity of the electric field received by the receiving portion 22B corresponds with or is proportional to the concentration of water or moisture within the material 19. In this manner, the capacitance sensor 22 can detect the concentration of moisture within the material 19.

The embedded moisture detection system 60 includes a controller 62 with a plurality of modules 64, 66, 68. The module 64 is a control module configured to control operation of the capacitance sensor 22. For example, the control module 64 may be in data transmitting communication with the transmitting portion 22A via a communication line 70, which can be a wired or wireless communication line. Further, the communication line 70 may also function as a power line to provide power for operation of the sensor 22. Alternatively, one or more separate power lines may be used for powering the sensor 22. Generally, the control module 64 commands the transmitting portion 22A to generate and transmit the electric field 50 with the characteristics associated with absorption in or blockage by moisture in the material 19. The receiving portion 22B transmits data representing the characteristics of the energy field 50 received from the transmitting portion 22A back to the controller 62 via a data communication line 72, which can be the same as or different than the data communication line 70.

The module 66 is a moisture determination module that receives the data from the receiving portion 22B, determines the energy of the received electric field 50 based on the data, and compares the energy of the received electric field to the energy of the transmitted electric field. In one implementation, the moisture determination module 66 compares the difference between the respective energies of the received and transmitted electric fields to one or more look-up tables containing predetermined moisture characteristics (e.g., absorption or concentration levels, percent saturation levels, and the like) for various energy differences. In this manner, the moisture determination module 66 determines the moisture characteristics of the material 19.

For embodiments having a plurality of sensors 22, the moisture determination module 66 is capable of determining the moisture characteristics of the material 19 at a plurality of locations. Accordingly, based on the plurality of moisture characteristics data points, the moisture determination module 66 is operable to determine a moisture concentration pattern across the portion of the aircraft 10 being analyzed. Further, based on the moisture concentration pattern, the moisture determination module 66 can determine moisture ingression locations on the aircraft 10. For example, a moisture concentration pattern with a grouping of high moisture concentration values around a localized area likely indicates a point of water ingression at that area. Alternatively, a single moisture concentration above a predetermined threshold at a given location may also indicate a point of water ingression at that location. If desired, the structure at the point of water ingression can be repaired if defective, or redesigned to prevent future water ingression.

The controller 62, including the moisture determination module 66, may contain memory for storing the raw sensor data received from the sensor 22 via the data communication line 72, and in some implementations for storing the moisture characteristics of the material 19 determined over time. In some embodiments, the module 68 of the controller 62 is a transmission module configured to transmit raw data or determined moisture characteristics to other computing devices for storage, processing, or further analysis. For example, in one implementation, the controller 62 is mounted on (e.g., forms part of an on-board diagnostic controller of) the aircraft 10, and the transmission module 68 transmits data collected by the sensor or sensors 22 to a computing device separate (e.g., remote) from the aircraft. The transmission module 68 may transmit the data via a wireless or wired data connection. In yet some implementations, the controller 62 can be separate from the aircraft, and even located remotely from the aircraft.

Referring back to FIG. 1, a non-embedded moisture detection system 30 is operable to detect moisture characteristics of material forming the aircraft 10. The system 30 includes a moisture detection sensor 32 positioned adjacent the exterior surfaces of an analyzed portion (e.g., horizontal stabilizer 18) of the aircraft 10. In other words, the moisture detection sensor 32 is not embedded in the material being analyzed, but rather is positioned externally from, and in close proximity with, the material being analyzed. As indicated by directional arrows 33 in FIG. 1, because the sensor 32 is not embedded into the aircraft 10, the sensor 32 can be movable along or about the exterior surface of the material being analyzed in any of various directions. The sensor 32 can be any of various types of moisture detection sensors, such as a capacitance sensors, microwave sensors, spectra response sensors, and the like, configured to detect the concentration of moisture within or on the material of a complex system, such as the aircraft 10. As the sensor 32 moves along the exterior surface of the aircraft, such as via manual operation of an operator or automatically-controlled machine, the sensor detects moisture concentrations within or on the material forming the aircraft 10 at various locations along the aircraft.

Moisture concentration information or data detected by the sensor 32 as it moves along the exterior surface of the aircraft 10 is transmitted via a data communication line 34 to a controller, which is depicted as the controller 36. The data communication line 34 can be a wireless signal encoded with the detected moisture concentration information as discussed above. Accordingly, the sensor 32 may have a wireless transmitter and the controller 36 may have a wireless receiver. Alternatively, the data communication line 34 may be a wired communication line (e.g., cable or wire) using a wired data communication protocol.

The controller 36 of the non-embedded moisture detection system 30 is configured as described above to store, process, and/or analyze the moisture concentration data received from the sensor 32. For example, the controller 36 may be configured to determine moisture characteristics (e.g., moisture saturation or diffusion within the material or moisture levels on the surface of the material) based on the moisture concentration data received from the sensor 32. The controller can then compare the moisture concentration data or determined moisture characteristics derived from the sensor 32 to predetermined thresholds, and generate a moisture condition status indicator or trigger a fault based on the comparison. The controller 36 may also be able to transmit the moisture concentration data from the sensor 32 to a local or remote computing device for initial or additional storage, processing, and/or analyzing.

The controller 36 is shown as forming part of both the embedded and non-embedded moisture detection systems 20, 30 mainly for convenience in depicting the subject matter of the present disclosure. For example, in certain embodiments, each moisture detection system 20, 30 includes its own independently-operable controller. Nevertheless, in some embodiments, each system 20, 30 may use the same controller if desired. For example, in some embodiments, both systems 20, 30 may be controlled by a single controller to independently detect moisture characteristics of a material forming the aircraft. The moisture characteristics of the material detected by the two systems using different detection techniques can then be compared (e.g., averaged) by the controller for more precisely estimating the moisture characteristics of the material. In one embodiment, for example, the controller may utilize first moisture characteristic data obtained from one or more sensors 22 of the system 20 and second moisture characteristic data obtained from one or more sensors 32 of the system 30 to determine the moisture characteristics or condition of the material. In yet another embodiment, for example, the system 30 may include multiple sensors 32 of differing types (e.g., one microwave sensor and one spectra sensor) to obtain moisture characteristic data using two different moisture detection techniques. The data obtained from one sensor can be compared to data obtained from the other sensor to more precisely estimate the moisture characteristics of the material.

In certain implementations, the non-embedded sensor 32 is movable to detect moisture concentrations at multiple locations of the aircraft 10 and transmits the detected moisture concentration information or data to the controller 36. Because the sensors 32 can detect the moisture concentration at various locations within a section of the aircraft, the controller 36 can utilize the multiple moisture concentration readings detected by the sensor 32 to determine advanced moisture characteristics of the material, such as moisture ingression sites, in a manner similar to embedded moisture detection systems with a plurality of embedded sensors.

Figure 3:
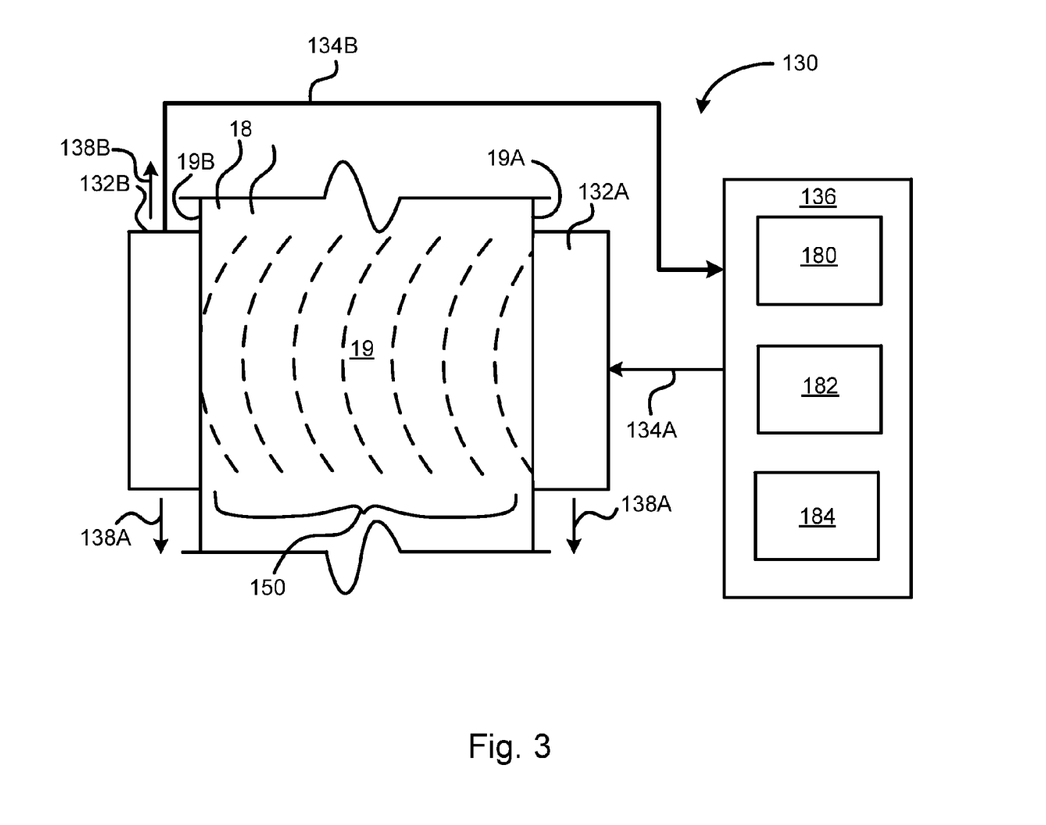
FIG. 3 is a schematic block diagram of a non-embedded moisture detection system according to one embodiment.

As shown in FIG. 3, according to one embodiment of a non-embedded moisture detection system 130, the non-embedded sensor 32 can be a capacitance sensor with a transmitting portion 132A and a receiving portion 132B that is spaced apart from the transmitting portion. Both the transmitting portion 132A and receiving portion 132B are positioned adjacent respective outermost and innermost surfaces 19A, 19B of a material forming a complex structure, which can be a composite material 19 forming the horizontal stabilizer 18 of the aircraft 10. As defined herein, adjacent may mean in contact with or in close proximity to an object. In some implementations, the innermost surface 19B may be an opposing outermost surface such that the non-embedded sensor portions 132A, 132B both are positioned adjacent outermost or exterior surfaces of the aircraft 10, and the material 19 may include a hollow or non-hollow interior sandwiched between dual outer layers of the material. Accordingly, similar to the embedded sensor portions 22A, 22B of FIG. 2, the non-embedded sensor portions 132A, 132B may be configured to detect moisture characteristics of multiple layers made from the same or different materials. Further, the non-embedded sensor 32 can detect moisture characteristics at various locations along the aircraft 10 by synchronously moving the sensor portions 132A, 132B along (e.g., parallel to) the surfaces 19A, 19B as indicated by directional arrows 138A, 138B.

The transmitting portion 132A and receiving portion 132B form part of a capacitance sensor 32. Similar to the capacitance sensor 22, the capacitance sensor 32 is configured to detect the concentration of moisture in the material 19 between the transmitting and receiving portions 132A, 132B. As shown, the transmitting portion 132A generates an electric field 150 and transmits the field through the material 19. After passing through the material 19, the transmitted electric field 150 is received by the receiving portion 132B. The characteristics (e.g., wavelength) of the electric field 150 are selected or tuned to correspond with an absorption property of water. In other words, the electric field 150 is configured to be absorbed by water within the material 19, which prevents the reception of the absorbed portion of the electric field by the receiving portion 132B. Following that described above, the difference between the energy or intensity of the electric field 150 transmitted by the transmitting portion 132A and the energy or intensity of the electric field received by the receiving portion 132B corresponds with or is proportional to the concentration of water or moisture within the material 19. In this manner, the capacitance sensor 32 can detect the concentration of moisture within the material 19.

The non-embedded moisture detection system 130 includes a controller 136 with a plurality of modules 180, 182, 184. The module 180 is a control module configured to control operation of the capacitance sensor 32. For example, the control module 180 may be in data transmitting communication with the transmitting portion 132A via a communication line 134A, which can be a wired or wireless communication line. Further, the communication line 134A may also function as a power line to provide power for operation of the sensor 32. Alternatively, one or more separate power lines may be used for powering the sensor 32. Generally, the control module 180 commands the transmitting portion 132A to generate and transmit the electric field 150 with the characteristics associated with absorption in or blockage by moisture in the material 19. The receiving portion 132B transmits data representing the characteristics of the energy field 150 received from the transmitting portion 132A back to the controller 136 via a data communication line 134B, which can be the same as or different than the data communication line 134A.

The module 182 is a moisture determination module that receives the data from the receiving portion 132B, determines the energy of the received electric field 150 based on the data, and compares the energy of the received electric field to the energy of the transmitted electric field. In one implementation, the moisture determination module 182 compares the difference between the respective energies of the received and transmitted electric fields to one or more look-up tables containing predetermined moisture characteristics (e.g., absorption or concentration levels, percent saturation levels, and the like) for various energy differences. In this manner, the moisture determination module 182 determines the moisture characteristics of the material 19.

For embodiments utilizing the mobility of the sensor 32 to determine the moisture characteristics of the material 19 at a plurality of locations, based on the plurality of moisture characteristics data points, the moisture determination module 182 is operable to determine a moisture concentration pattern across the portion of the aircraft 10 being analyzed. Further, based on the moisture concentration pattern, the moisture determination module 182 can determine moisture ingression locations on the aircraft 10 according to various implementations, such as those described above associated with the moisture determination module 66. The controller 136, including the moisture determination module 182, may contain memory for storing the raw sensor data received from the sensor 32 via the data communication line 134B, and in some implementations for storing the moisture characteristics of the material 19 determined over time.

In some embodiments, the module 184 of the controller 136 is a transmission module configured to transmit raw data or determined moisture characteristics to other computing devices for storage, processing, or further analysis. For example, in one implementation, the controller 136 is mounted on (e.g., forms part of an on-board diagnostic controller of) the aircraft 10, and the transmission module 184 transmits data collected by the sensor 32 to a computing device separate (e.g., remote) from the aircraft. The transmission module 184 may transmit the data via a wireless or wired data connection. In yet some implementations, the controller 136 can be separate from the aircraft, and even located remotely from the aircraft.

Figure 4:
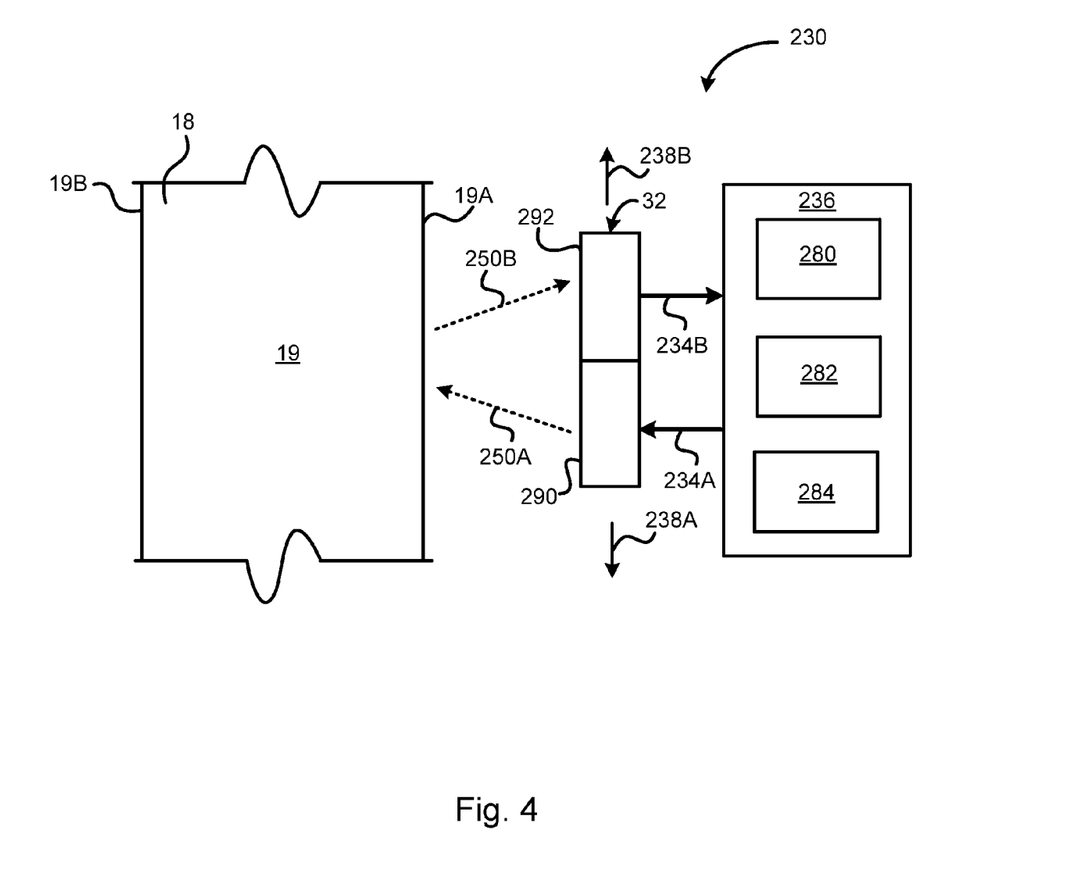
FIG. 4 is a schematic block diagram of a non-embedded moisture detection system according to yet another embodiment.

As shown in FIG. 4, according to another embodiment of a non-embedded moisture detection system 230, the non-embedded sensor 32 can be a sensor 32 for detecting moisture on a surface of a material, such as a microwave or spectra response sensor. The sensor 32 includes a transmitting portion 290 and a receiving portion 292. The transmitting and receiving portions 290, 292 can be adjacent each other in a side-by-side configuration as shown, or some other configuration as desired. Both the transmitting portion 290 and receiving portion 292 are positioned adjacent an outermost surface 19A of the material 19 to detect moisture characteristics on the outermost surface. As defined in this particular embodiment, adjacent means spaced-apart from, but in close proximity to, an object. In some implementations, the transmitting and receiving portions 290, 292 can be adjacent an innermost surface 19B to detect moisture characteristics on the innermost surface. The non-embedded sensor 32 can detect moisture characteristics at various locations along the aircraft 10 by moving the sensor, including the portions 290, 292 along (e.g., parallel to) the surfaces 19A, 19B as indicated by directional arrows 238A, 238B.

In one embodiment, the transmitting portion 290 and receiving portion 292 form part of a microwave sensor 32. The microwave sensor 32 is configured to detect the concentration of moisture on the material 19. As shown, the transmitting portion 290 generates an electromagnetic energy field 250A or microwave pulse or beam, and transmits the field to the outermost surface 19A of the material 19. Because water is a highly conductive material, the portion of the electromagnetic energy field 250A contacting water is reflected back away from the outermost surface. The remaining portion of the electromagnetic energy field 250A is absorbed by the material 19. After reflecting off of moisture on the surface of the material 19, the reflected electromagnetic field 250B is received by the receiving portion 292. The concentration or quantity of microwaves or energy of the reflected electromagnetic field 250B and received by the receiving portion 292 corresponds directly with the concentration or quantity of moisture on the surface. The characteristics (e.g., wavelength and/or intensity) of the electromagnetic field 250A are selected or tuned to correspond with a reflective property of water. In other words, the electromagnetic field 250A is configured to be reflected by water on the material 19 and absorbed by the material, with the reflected portion of the electric field being received and quantified the receiving portion 292.

In a similar embodiment, the transmitting portion 290 and receiving portion 292 form part of a spectra sensor 32 or spectrameter. Like the microwave sensor, the spectra sensor 32 also is configured to detect the concentration of moisture on the material 19. However, the transmitting portion 290 generates a beam or field of light 250A, and transmits the light beam to the outermost surface 19A of the material 19. Because water has a specific light-refraction signature, the beam of light 250B reflected from water on the outermost surface exhibits a unique light-refraction signature. After reflecting off of moisture on the surface of the material 19, the reflected beam of light 250B is received by the receiving portion 292. The receiving portion 292 is configured to detect the light-refraction signatures of the reflected beam of light 250B and determine the concentration or quantity of moisture on the surface based on the concentration or quantity of light-refraction signatures associated with moisture in the beam of light received by the receiving portion 292.

Although the moisture detection sensors of the illustrated embodiments have been described as being one of a capacitance, microwave, or spectra sensor, in other embodiments, the moisture detection sensor of the moisture detection systems described herein can be other types of similar or dissimilar sensors, such as voltage, resistance, or impedance sensors.

Whether the sensor 32 is a microwave sensor, spectra sensor, or other similar sensor that emits and receives a beam of energy, the non-embedded moisture detection system 230 includes a controller 236 with a plurality of modules 280, 282, 284. The module 280 is a control module configured to control operation of the sensor 32. For example, the control module 280 may be in data transmitting communication with the transmitting portion 290 via a communication line 234A, which can be a wired or wireless communication line. Further, the communication line 234A may also function as a power line to provide power for operation of the sensor 32. Alternatively, one or more separate power lines may be used for powering the sensor 32. Generally, the control module 280 commands the transmitting portion 290 to generate and transmit the electromagnetic field 250A for embodiments with a microwave sensor 32, or the beam of light 250A for embodiments with a spectra sensor 32. The receiving portion 292 transmits data representing the characteristics of the reflected electromagnetic field or beam of light 250A received from the transmitting portion 290 back to the controller 236 via a data communication line 234B, which can be the same as or different than the data communication line 234A.

The module 282 is a moisture determination module that receives the surface moisture data from the receiving portion 292, and compares the data against one or more look-up tables containing predetermined moisture characteristics (e.g., concentration levels within the material, concentration levels on the exterior surface of the material, percent saturation levels, and the like) for various data values (e.g., reflected electromagnetic field values and light-refraction signature values). In this manner, the moisture determination module 282 determines the moisture characteristics of the material 19.

For embodiments utilizing the mobility of the sensor 32 to determine the moisture characteristics of the material 19 at a plurality of locations, based on the plurality of moisture characteristics data points, the moisture determination module 282 is operable to determine a moisture concentration pattern across the portion of the aircraft 10 being analyzed. Further, based on the moisture concentration pattern, the moisture determination module 282 can determine moisture ingression locations on the aircraft 10 according to various implementations, such as those described above associated with the moisture determination modules 66 and 182. The controller 236, including the moisture determination module 282, may contain memory for storing the raw sensor data received from the sensor 32 via the data communication line 234B, and in some implementations for storing the moisture characteristics of the material 19 determined over time.

In some embodiments, the module 284 of the controller 236 is a transmission module configured to transmit raw data or determined moisture characteristics to other computing devices for storage, processing, or further analysis. For example, in one implementation, the controller 236 is mounted on (e.g., forms part of an on-board diagnostic controller of) the aircraft 10, and the transmission module 284 transmits data collected by the sensor 32 to a computing device separate (e.g., remote) from the aircraft. The transmission module 284 may transmit the data via a wireless or wired data connection. In yet some implementations, the controller 236 can be separate from the aircraft, and even located remotely from the aircraft.

Figure 5:
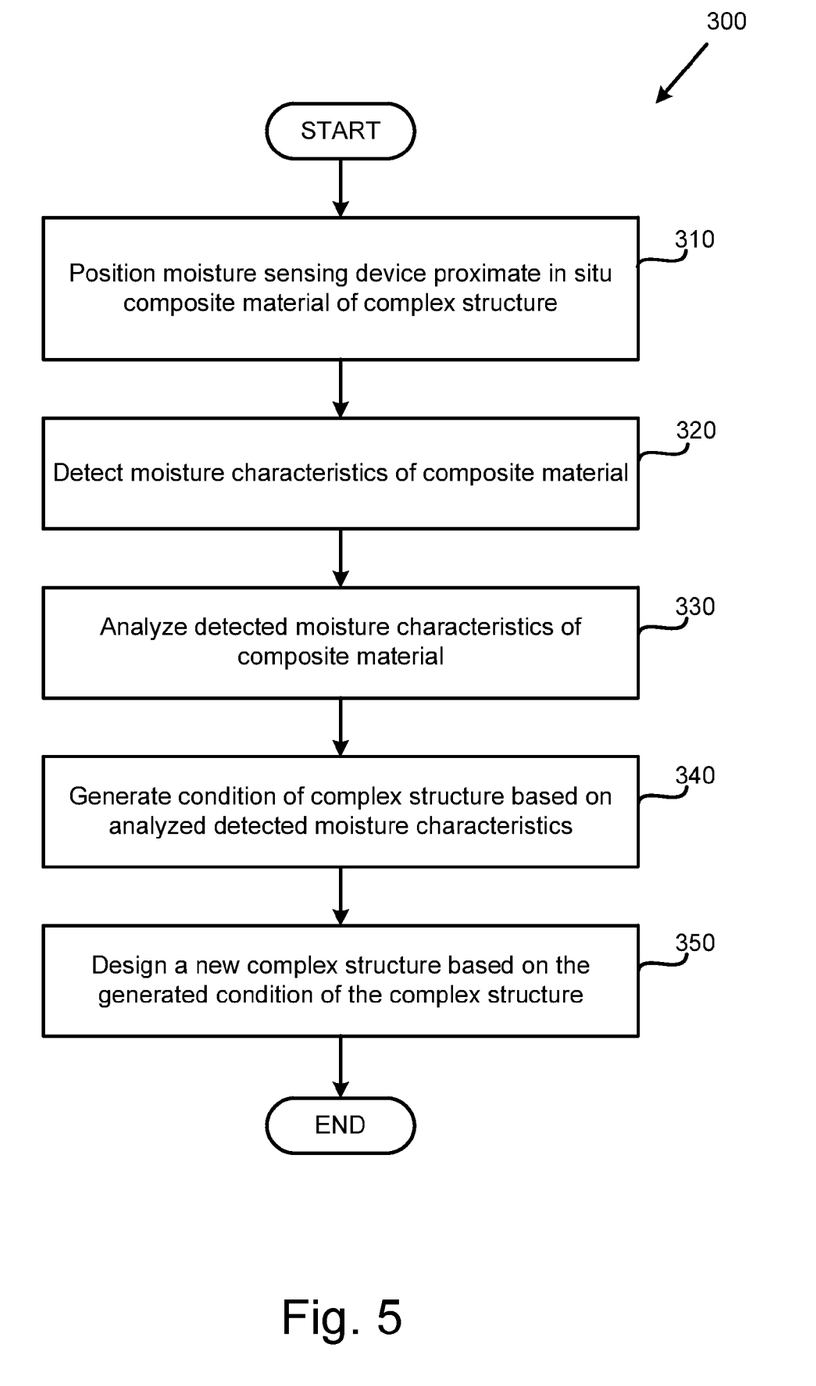
FIG. 5 is a schematic flow chart diagram illustrating a method for detecting moisture characteristics of a material according to one embodiment.

Referring to FIG. 5, a flowchart illustrates a method 300 for detecting moisture characteristics of a material through the use of a system such as the systems 20, 30, 60, 130, 230 of FIGS. 1-4. In alternative embodiments, the method 300 may be carried out through the use of a system (not shown) different from the systems described above. Alternatively, the systems 20, 30, 60, 130, 230 of FIGS. 1-4 may be used with a method (not shown) different from the method 300.

The method 300 starts at step 310 by positioning one or more moisture sensing devices proximate an in situ composite material of a complex structure, such as the aircraft 10. The moisture sensing device or devices is used to detect moisture characteristics of the composite material at step 320. The moisture characteristics detected by the moisture sensing device can be raw data that is later analyzed at step 330 by a moisture determination module or similar module. The method 300 may also generate a condition of the complex structure based on the detected data analyzed at step 340. The condition of the complex structure may include an indication of the moisture characteristics of the complex structure compared to fault thresholds. For example, the condition of the complex structure may be one of an acceptable identifier or failure identifier. Based on the condition of the complex structure, or the detected moisture characteristics, the method 300 includes designing a new complex structure or repairing a damaged or defective portion of the existing structure at step 350. The new complex structure may be design to mitigate moisture saturation or ingression points identified at steps 330 and/or 340. In certain implementations, the method 300 may include disuse of the complex structure (e.g., grounding the aircraft 10) should the generated condition of the complex structure indicate severe moisture saturation conditions or ingression, such as moisture saturation conditions or ingressions above a predetermined maximum allowable threshold.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model.

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally the accessed server may make requests of other servers that require CPU units. CPU units are an example that represents but one measurement of use. Other measurements of use include but are not limited to network bandwidth, memory usage, storage usage, packet transfers, complete transactions etc.

Aspects of the embodiments may be described above with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A system for detecting moisture characteristics of a material of a complex structure while the material is in situ, comprising:
   at least one moisture detection sensor embedded in the material of the complex structure while the material is in situ; and
   a controller in data receiving communication with the at least one moisture detection sensor;
   wherein the at least one moisture detection sensor comprises a transmitting portion embedded in the material on an exterior surface of the material and a receiving portion embedded in the material on an interior surface of the material, the material having a thickness defined between the interior and exterior surfaces, the transmitting portion being spaced apart from the receiving portion across the thickness of the material with the material being interposed between the transmitting portion and the receiving portion, wherein the transmitting portion transmits an electromagnetic microwave pulse through the thickness of the material interposed between the transmitting portion and the receiving portion, and the receiving portion receives the electromagnetic microwave pulse from the transmitting portion after being transmitted through the material interposed between the transmitting portion and the receiving portion; and
   wherein the electromagnetic microwave pulse is tuned responsive to an electromagnetic-energy absorption property of moisture.

2. The system of claim 1, wherein the controller is in data receiving communication with the at least one moisture detection sensor via a wireless connection.

3. The system of claim 1, wherein the at least one moisture detection sensor comprises a plurality of moisture detection sensors.

4. The system of claim 1, wherein the controller determines at least one of a moisture saturation level of the material, or a moisture ingression point in the material.

5. The system of claim 1, wherein the material comprises a composite material.

6. The system of claim 5, wherein the complex structure comprises an aircraft.

7. The system of claim 1, wherein the at least one moisture detection sensor comprises a first moisture detection sensor of a first type and a second moisture detection sensor of a second type different than the first type, and wherein the controller is in data receiving communication with the first and second moisture detection sensors.

8. The system of claim 1, wherein the at least one moisture detection sensor comprises at least one of a capacitance sensor, microwave sensor, or spectra sensor.

9. The system of claim 1, wherein the controller is coupled to the complex structure.

10. The system of claim 1, wherein the at least one moisture detection sensor detects moisture in real-time during operation of the complex structure, and transmits moisture data to the controller in real-time during operation of the complex structure.

11. A system for detecting moisture characteristics, comprising:
   an operational aircraft comprising a body made from a composite material;
   at least one moisture detection sensor completely embedded within the composite material of the operational aircraft, wherein the at least one moisture detection sensor detects moisture characteristics of the composite material of the operational aircraft, wherein the at least one moisture detection sensor comprises a transmitting portion embedded in the material on an exterior surface of the material and a receiving portion embedded in the material on an interior surface of the material, the material having a thickness defined between the interior and exterior surfaces, the transmitting portion being spaced apart from the receiving portion across the thickness of the material with the material being interposed between the transmitting portion and the receiving portion, wherein the transmitting portion transmits an electromagnetic microwave pulse through the thickness of the material interposed between the transmitting portion and the receiving portion, and the receiving portion receives the electromagnetic microwave pulse from the transmitting portion after being transmitted through the material interposed between the transmitting portion and the receiving portion; and
   a controller that receives moisture characteristics from the at least one moisture detection sensor and determines a condition of the material based on the moisture characteristics;
   wherein the at least one moisture detection sensor detects moisture in real-time during flight of the operational aircraft, and transmits moisture data to the controller in real-time during flight of the operational aircraft.

12. The system of claim 11, wherein the condition comprises at least one of a moisture saturation level of the material, a moisture concentration level on a surface of the material, or a moisture ingression point in the material.

13. A method for detecting moisture characteristics of a material of an operational complex structure, comprising:
   positioning a plurality of moisture sensing devices proximate a material of the operational complex structure while the complex structure is operational, the material having a thickness defined between opposing interior and exterior surfaces;
   detecting moisture characteristics of the material with the moisture sensing devices; and
   determining a condition of the operational complex structure based on the moisture characteristics;
   wherein the plurality of moisture sensing devices each comprises a transmitting portion and a receiving portion, and positioning the plurality of moisture sensing devices proximate the material of the operational complex structure while the complex structure is operational comprises embedding each transmitting portion of a respective moisture sensing device in the material such that the transmitting portion is completely enclosed by the material and inset from one of the interior and exterior surfaces of the material and embedding each receiving portion of the respective moisture sensing device in the material such that the receiving portion is completely enclosed by the material and inset from the other of the interior and exterior surfaces of the material such that each transmitting portion of the respective moisture sensing device is spaced apart from each receiving portion of the respective moisture sensing device across the thickness of the material with the material being interposed between the transmitting portion and the receiving portion of the respective moisture sensing device;

wherein detecting moisture characteristics of the material with the moisture sensing device comprises transmitting from the transmitting portion of a respective moisture sensing device an electromagnetic microwave pulse through the thickness of the material interposed between the transmitting portion and the receiving portion of the respective moisture sensing device, and receiving with the receiving portion of the respective moisture sensing device the electromagnetic microwave pulse from the transmitting portion after being transmitted through the material interposed between the transmitting portion and the receiving portion of the respective moisture sensing device; and wherein the method further comprises tuning the electromagnetic microwave pulse responsive to an electromagnetic energy absorption property of moisture.

* * * * *